(12) United States Patent
Bernotas et al.

(10) Patent No.: US 7,057,039 B2
(45) Date of Patent: Jun. 6, 2006

(54) 1-HETEROCYCLYLALKYL-3-SULFONYLAZAINDOLE OR -AZAINDAZOLE DERIVATIVES AS 5-HYDROXYTRYPTAMINE-6 LIGANDS

(75) Inventors: Ronald Charles Bernotas, Bridgewater, NJ (US); Steven Edward Lenicek, Plainsboro, NJ (US); Hassan Mahmoud Elokdah, Yardley, PA (US); David Zenan Li, Princeton, NJ (US)

(73) Assignee: Wyeth, Madison, NJ (US)

( * ) Notice: Subject to any disclaimer, the term of this patent is extended or adjusted under 35 U.S.C. 154(b) by 189 days.

(21) Appl. No.: 10/621,432

(22) Filed: Jul. 17, 2003

(65) Prior Publication Data

US 2004/0023970 A1     Feb. 5, 2004

Related U.S. Application Data

(60) Provisional application No. 60/396,949, filed on Jul. 18, 2002.

(51) Int. Cl.
  *C07D 413/00*   (2006.01)
  *A01N 43/64*    (2006.01)
  *A61K 31/41*    (2006.01)

(52) U.S. Cl. ............... 544/125; 544/126; 514/359; 514/360

(58) Field of Classification Search ........ 544/125, 544/126; 514/359, 360
  See application file for complete search history.

(56) References Cited

U.S. PATENT DOCUMENTS

6,187,777 B1   2/2001   Norman et al.
6,187,805 B1   2/2001   Pineiro et al.
6,495,688 B1   12/2002  Yuan et al.

FOREIGN PATENT DOCUMENTS

WO   WO 97/49698 A1   12/1997
WO   WO/9749698    *  12/1997
WO   WO01/12629    *  2/2001
WO   WO 01/12629 A1   2/2001

* cited by examiner

*Primary Examiner*—James O. Wilson
*Assistant Examiner*—Paul V. Ward
(74) *Attorney, Agent, or Firm*—Barbara L. Lences

(57) ABSTRACT

The present invention provides a compound of formula I and the use thereof for the treatment of a central nervous system disorder related to or affected by the 5-HT6 receptor.

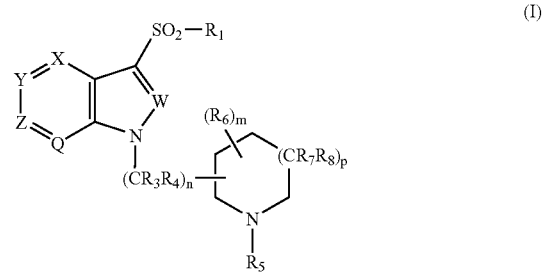

15 Claims, No Drawings

1-HETEROCYCLYLALKYL-3-SULFONYLAZAINDOLE OR -AZAINDAZOLE DERIVATIVES AS 5-HYDROXYTRYPTAMINE-6 LIGANDS

BACKGROUND OF THE INVENTION

This application claims priority from copending provisional application Ser. No. 60/396,949, filed Jul. 18, 2002, the entire disclosure of which is hereby incorporated by reference.

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320–327) and subsequently from human tissue (Kohen, R.; Metcalf, M. A.; Khan, N.; Druck, T.; Huebner, K.; Sibley, D. R. *Journal of Neurochemistry* 1996, 66, 47–56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268–276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105–1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; E I Mestikawy, S. *Brain Research*, 1997, 746, 207–219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537–1542). Studies have found that a known 5-HT6 selective antagonist significantly increased glutamate and aspartate levels in the frontal cortex without elevating levels of noradrenaline, dopamin, or, 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology*, 2000, 130(1), 23–26). Animal studies of memory and learning with a known selective 5-HT6 antagonist found some positive effects (Rogers, D. C.; Hatcher, P. D.; Hagan, J. J. *Society of Neuroscience*, Abstracts 2000, 26, 680).

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901–5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319–334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606–1612).

Taken together, the above studies strongly suggest that compounds which are 5-HT6 receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a 1-heterocyclylalkyl-3-sulfonylazaindole or -azaindazole compound of formula I (I)

[Chemical structure diagram showing formula (I) with SO₂—R₁, ring system with W, X, Y, Z, Q, substituents (R₆)ₘ, (CR₃R₄)ₙ, (CR₇R₈)ₚ, and N-R₅]

wherein
- W is N or $CR_2$;
- X is N or $CR_9$;
- Y is N or $CR_{10}$;
- Z is N or $CR_{11}$;
- Q is N or $CR_{12}$ with the proviso that at least one and not more than two of X, Y, Z and Q must be N;
- $R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
- $R_2$ is H, halogen, or a $C_1$–$C_6$alkyl, $C_1$–$C_6$alkoxy, $C_3$–$C_7$cycloalkyl, aryl or heteroaryl group each optionally substituted;
- $R_3$ and $R_4$ are each independently H or an optionally substituted $C_1$–$C_6$alkyl group;
- $R_5$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
- $R_6$ is a $C_1$–$C_6$alkyl, $C_3$–$C_7$cycloalkyl, $C_2$–$C_6$alkenyl or $C_2$–$C_6$alkynyl group each optionally substituted;
- $R_7$ and $R_8$ are each independently H or a $C_1$–$C_6$alkyl, $C_3$–$C_7$cycloalkyl, $C_2$–$C_6$alkenyl or $C_2$–$C_6$alkynyl group each optionally substituted;
- m and n are each independently 0 or an integer of 1, 2 or 3;
- p is 0 or an integer of 1 or 2;
- $R_9$, $R_{10}$, $R_{11}$ and $R_{12}$ are each independently H, halogen, CN, $OCO_2R_{13}$, $CO_2R_{14}$, $CONR_{15}R_{16}$, $SO_xR_{17}$, $NR_{18}R_{19}$, $OR_{20}$, $COR_{21}$ or a $C_1$–$C_6$alkyl, $C_2$–$C_6$alkenyl, $C_2$–$C_6$alkynyl, $C_3$–$C_7$cycloalkyl, aryl or heteroaryl group each optionally substituted;
- $R_{13}$, $R_{14}$, $R_{17}$ and $R_{21}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
- $R_{15}$, $R_{16}$, $R_{18}$ and $R_{19}$ are each independently H or an optionally substituted $C_1$–$C_4$alkyl group or $R_{15}$ and $R_{16}$ or $R_{18}$ and $R_{19}$ may be taken together with the atom to which they are attached to form a 5- to 7-membered ring optionally containing another heteroatom selected from O, $NR_{22}$ or $SO_q$;
- $R_{20}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
- x and q are each independently 0 or an integer of 1 or 2; and
- $R_{22}$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or heteraryl group each optionally substituted; or the stereoisomers thereof or the pharmaceutically acceptable salts thereof.

The present invention also provides methods and compositions useful for the therapeutic treatment of a central nervous system disorder related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that 1-heterocyclylalkyl-3-sulfonylazaindole and -azaindazole derivatives of formula I demonstrate 5-HT6 affinity. Advantageously, said azaindole and azaindazole derivatives may be used as effective therapeutic agents for the treatment of central nervous system (CNS) disorders associated with or affected by the 5-HT6 receptor. Accordingly, the present invention provides 1-heterocyclylalkyl-3-sulfonylazaindole and -azaindazole derivatives of formula I (I)

[Chemical structure diagram of formula (I)]

wherein
- W is N or $CR_2$;
- X is N or $CR_9$;
- Y is N or $CR_{10}$;
- Z is N or $CR_{11}$;
- Q is N or $CR_{12}$ with the proviso that at least one and not more than two of X, Y, Z and must be N;
- $R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
- $R_2$ is H, halogen, or a $C_1$–$C_6$alkyl, $C_1$–$C_6$alkoxy, $C_3$–$C_7$cycloalkyl, aryl or heteroaryl group each optionally substituted;

$R_3$ and $R_4$ are each independently H or an optionally substituted $C_1$–$C_6$alkyl group;

$R_5$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

$R_6$ is a $C_1$–$C_6$alkyl, $C_3$–$C_7$cycloalkyl, $C_2$–$C_6$alkenyl or $C_2$–$C_6$alkynyl group each optionally substituted;

$R_7$ and $R_8$ are each independently H or a $C_1$–$C_6$alkyl, $C_3$–$C_7$cycloalkyl, $C_2$–$C_6$alkenyl or $C_2$–$C_6$alkynyl group each optionally substituted;

m and n are each independently 0 or an integer of 1, 2 or 3;

p is 0 or an integer of 1 or 2;

$R_9$, $R_{10}$, $R_{11}$ and $R_{12}$ are each independently H, halogen, CN, $OCO_2R_{13}$, $CO_2R_{14}$, $CONR_{15}R_{16}$, $SO_xR_{17}$, $NR_{18}R_{19}$, $OR_{20}$, $COR_{21}$ or a $C_1$–$C_6$alky, $C_2$–$C_6$alkenyl, $C_2$–$C_6$alkynyl, $C_3$–$C_7$cycloalkyl, aryl or heteroaryl group each optionally substituted;

$R_{13}$, $R_{14}$, $R_{17}$ and $R_{21}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{15}$, $R_{16}$, $R_{18}$ and $R_{19}$ are each independently H or an optionally substituted $C_1$–$C_4$alkyl group or $R_{15}$ and $R_{16}$ or $R_{18}$ and $R_{19}$ may be taken together with the atom to which they are attached to form a 5- to 7-membered ring optionally containing another heteroatom selected from O, $NR_{22}$ or $SO_q$;

$R_{20}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

x and q are each independently 0 or an integer of 1 or 2; and $R_{22}$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or hetaryl group each optionally substituted; or the stereoisomers thereof or the pharmaceutically acceptable salts thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein $W_2$ is NR, O or S; and R is H or an optional substituent as described hereinbelow:

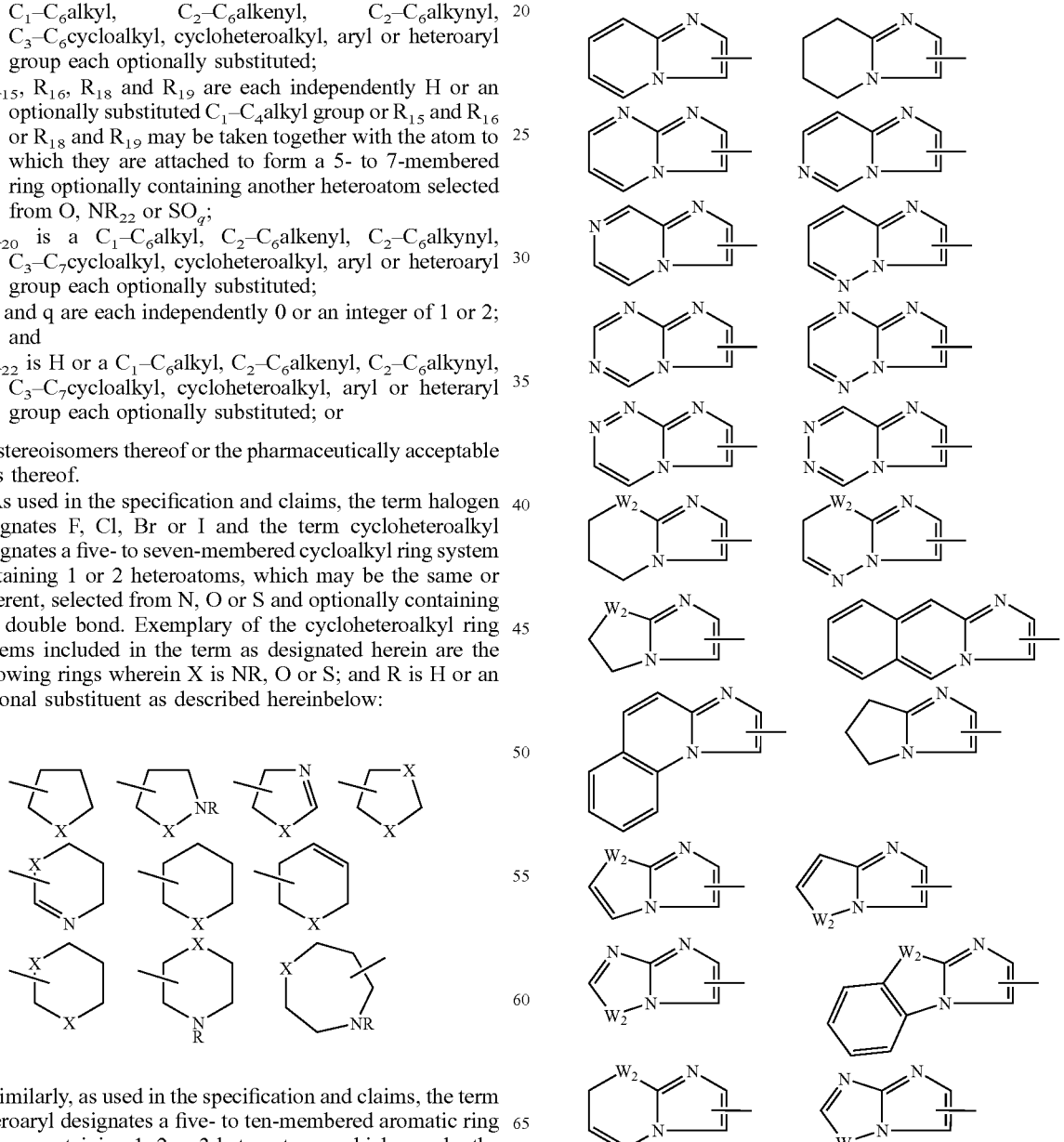

-continued

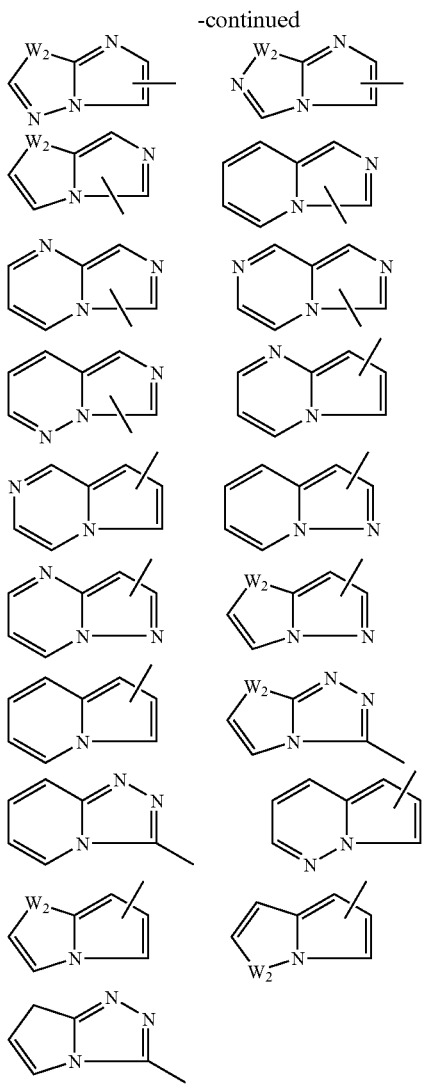

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl as designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein n is 0 or 1. Also preferred are those compounds of formula I wherein $R_5$ is H or methyl. Another group of preferred compounds of formula I are those compounds wherein $R_1$ is an optionally substituted phenyl, thienyl or imidazothiazolyl group.

More preferred compounds of the invention are those formula I compounds wherein n is 0 or 1 and p is 0 or 1. Another group of more preferred compounds are those formula I compounds wherein n is 0 or 1 and m is 0. Further more preferred formula I compounds are those compounds wherein n is 0 or 1; p is 0 or 1; and the piperidinyl group is attached in the 3-position of the piperidine ring or the pyrrolidinyl group is attached in the 2-position of the pyrrolidine ring.

Examples of preferred compounds of formula I include:
3-(phenylsulfonyl)-1-[(2R)-pyrrolidin-2-ylmethyl]-1H-pyrrolo[2,3-b]pyridine;
3-(phenylsulfonyl)-1-[(2S)-pyrrolidin-2-ylmethyl]-1H-pyrrolo[2,3-b]pyridine;
3-[(4-methylphenyl)sulfonyl]-1-(piperidin-4-ylmethyl)-1H-pyrrolo[2,3-b]pyridine;
6-bromo-3-(phenylsulfonyl)-1-(piperidin-4-ylmethyl)-1H-pyrrolo[2,3-c]pyridine;
4-chloro-3-(phenylsulfonyl)-1-(piperidin-4-ylmethyl)-1H-pyrazolo[4,3-b]pyridine;
7-methoxy-3-(phenylsulfonyl)-1-(piperidin-4-ylmethyl)-1H-pyrrolo[2,3-c]pyridine;
6-hydroxy-3-(phenylsulfonyl)-1-(piperidin-4-ylmethyl)-1H-pyrrolo[3,2-b]pyridine;
6-chloro-3-[(4-fluorophenyl)sulfonyl]-1-(piperidin-4-ylmethyl)-1H-pyrrolo[2,3-c]pyridine;
6-fluoro-3-[(3-fluorophenyl)sulfonyl]-1-(piperidin-4-ylmethyl)-1H-pyrrolo[3,2-b]pyridine;
5-chloro-3-[(3-chlorophenyl)sulfonyl]-1-(piperidin-4-ylmethyl)-1H-pyrrolo[3,2-c]pyridine;

3-[(2-chlorophenyl)sulfonyl]-6-fluoro-1-(piperidin-4-ylmethyl)-1H-pyrrolo[2,3-c]pyridine;
3-[(2-fluorophenyl)sulfonyl]-6-methoxy-1-(piperidin-4-ylmethyl)-1H-pyrrolo[3,2-b]pyridine;
4-chloro-3-(phenylsulfonyl)-1-(piperidin-3-ylmethyl)-1H-pyrrolo[2,3-b]pyridine;
7-methoxy-3-(phenylsulfonyl)-1-(piperidin-3-ylmethyl)-1H-pyrrolo[2,3-c]pyridine;
6-hydroxy-3-(phenylsulfonyl)-1-(piperidin-3-ylmethyl)-1H-pyrrolo[3,2-b]pyridine;
6-chloro-3-[(4-fluorophenyl)sulfonyl]-1-(piperidin-2-ylmethyl)-1H-pyrrolo[3,2-c]pyridine;
6-fluoro-3-[(3-fluorophenyl)sulfonyl]-1-(piperidin-2-ylmethyl)-1H-pyrrolo[2,3-b]pyridine;
5-chloro-3-[(3-chlorophenyl)sulfonyl]-1-(piperidin-2-ylmethyl)-1H-pyrrolo[2,3-c]pyridine;
3-[(2-chlorophenyl)sulfonyl]-6-fluoro-1-(piperidin-2-ylmethyl)-1H-pyrrolo[3,2-b]pyridine;
3-[(2-fluorophenyl)sulfonyl]-6-methoxy-1-(piperidin-2-ylmethyl)-1H-pyrrolo[3,2-c]pyridine;
3-(phenylsulfonyl)-1-(piperidin-4-ylmethyl)-1H-pyrazolo[4,3-b]pyridine;
3-(phenylsulfonyl)-1-(piperidin-3-ylmethyl)-1H-pyrazolo[4,3-c]pyridine;
3-(phenylsulfonyl)-1-(piperidin-2-ylmethyl)-1H-pyrazolo[4,3-b]pyridine;
3-(phenylsulfonyl)-1-(pyrrolidin-3-ylmethyl)-1H-pyrazolo[3,4-c]pyridine;
3-(phenylsulfonyl)-1-(pyrrolidin-2-ylmethyl)-1H-pyrazolo[3,4-b]pyridine;
6-bromo-3-(phenylsulfonyl)-1-(pyrrolidin-3-ylmethyl)-1H-pyrrolo[3,2-b]pyridine;
4-chloro-2-methyl-3-(phenylsulfonyl)-1-(pyrrolidin-2-ylmethyl)-1H-pyrrolo[2,3-b]pyridine;
7-methoxy-3-(phenylsulfonyl)-1-(pyrrolidin-2-ylmethyl)-1H-pyrrolo[2,3-c]pyridine;
6-hydroxy-3-(phenylsulfonyl)-1-(pyrrolidin-2-ylmethyl)-1H-pyrrolo[3,2-b]pyridine;
1-(piperidin-2-ylmethyl)-3-(2-pyridinylsulfonyl)-1H-pyrrolo[3,2-c]pyridine;
1-(piperidin-3-ylmethyl)-3-(2-pyridinylsulfonyl)-1H-pyrrolo[2,3-b]pyridine;
3-(2-pyridinylsulfonyl)-1-(pyrrolidin-3-ylmethyl)-1H-pyrrolo[2,3-c]pyridine;
1-(piperidin-3-ylmethyl)-3-(2-thienylsulfonyl)-1H-pyrazolo[4,3-b]pyridine;
1-(piperidin-2-ylmethyl)-3-(2-thienylsulfonyl)-1H-pyrazolo[4,3-b]pyridine;
3-(phenylsulfonyl)-1-piperidin-3-yl-1H-pyrazolo[4,3-b]pyridine;
3-[(2-fluorophenyl)sulfonyl]-1-pyrrolidin-3-yl-1H-pyrazolo[4,3-b]pyridine;
1-(1-methylpiperidin-4-yl)-3-(phenylsulfonyl)-1H-pyrazolo[4,3-b]pyridine;
1-(1-phenethylpyrrolidin-3-yl)-3-(phenylsulfonyl)-1H-pyrrolo[3,2-c]pyridine;
1-piperidin-4-yl-3-(2-pyridylsulfonyl)-1H-pyrrolo[2,3-c]pyridine;
1-piperidin-3-yl-3-(2-thienylsulfonyl)-1H-pyrrolo[3,2-b]pyridine;
1-pyrrolidin-3-yl-3-(3-thienylsulfonyl)-1H-pyrrolo[3,2-b]pyridine;
1-[(1-benzylpyrrolidin-2-yl)methyl]-3-(phenylsulfonyl)-1H-pyrrolo[2,3-b]pyridine;
3-(phenylsulfonyl)-1-(pyrrolidin-2-ylmethyl)-1H-pyrrolo[2,3-b]pyridine;
1-[(1-benzylpyrrolidin-2-yl)methyl]-3-(3-fluorophenylsulfonyl)-1H-pyrrolo[2,3-b]-pyridine;
3-(3-fluorophenylsulfonyl)-1-(pyrrolidin-2-ylmethyl)-1H-pyrrolo[2,3-b]pyridine;
1-[(1-benzylpyrrolidin-2-yl)methyl]-3-(3-chlorophenylsulfonyl)-1H-pyrrolo[2,3-b]-pyridine;
3-(3-chlorophenylsulfonyl)-1-(pyrrolidin-2-ylmethyl)-1H-pyrrolo[2,3-b]pyridine;
3-(3-chlorophenylsulfonyl)-1-[(1-methylpyrrolidin-2-yl)methyl]-1H-pyrrolo[2,3-b]pyridine;
3-[(6-chloroimidazo[2,1-b][1,3]thiazol-5-yl)sulfonyl]-1-(pyrrolidin-2-ylmethyl)-1H-pyrrolo[2,3-b]pyridine;
3-[(6-chloroimidazo[2,1-b][1,3]thiazol-5-yl)sulfonyl]-1-(1-methylpiperidin-3-yl))-1H-pyrrolo[2,3-b]pyridine;
3-[(6-chloroimidazo[2,1-b][1,3]thiazol-5-yl)sulfonyl]-1-(piperidin-3-yl))-1H-pyrrolo[2,3-b]pyridine;
3-[(6-chlorothien-2-yl)sulfonyl]-1-(pyrrolidin-2-ylmethyl)-1H-pyrrolo[2,3-b]pyridine;

the stereoisomers thereof; or the pharmaceutically acceptable salts thereof.

Advantageously, the present invention provides a process for the preparation of a compound of formula I which comprises reacting a compound of formula II with a protected azacyclic compound of formula III in the presence of a first base to give the protected compound of formula IV and deprotecting said formula IV compound in the presence of an acid to give the free amine compound of formula I wherein $R_5$ is H optionally reacting said free amine with a compound, $R_5$-L', wherein L' is a leaving group such as halogen, in the presence of a second base. The process is illustrated in flow diagram I wherein L and L' represent a leaving group and P represents a protecting group.

Flow Diagram I

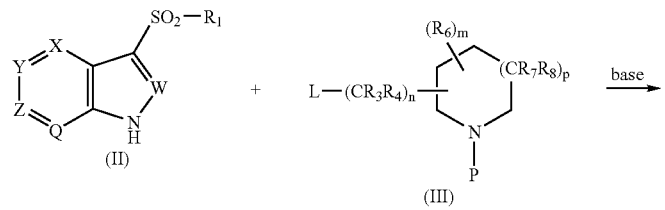

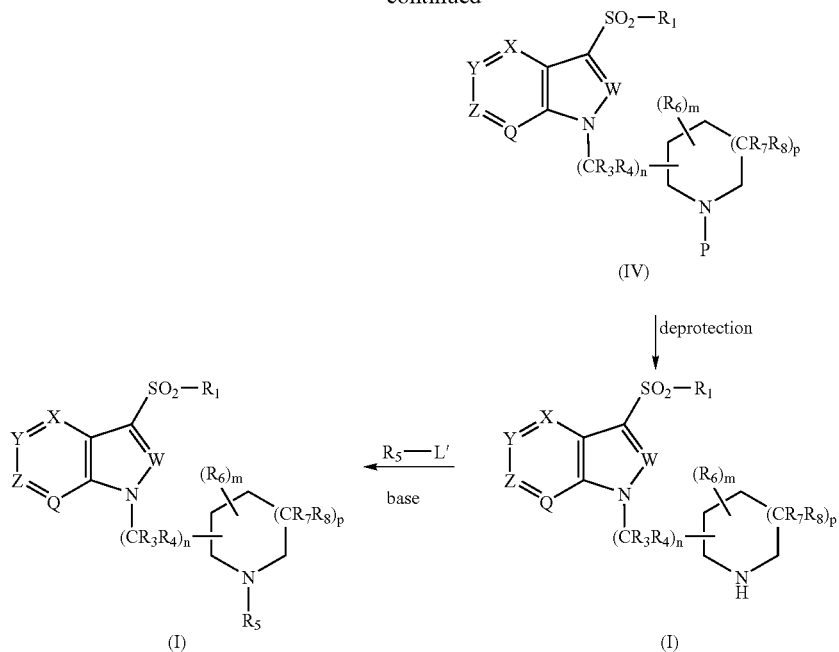

Protecting groups suitable for use in the process of the invention include t-butylcarboxylate, benzyl, acetyl, benzyloxycarbonyl, or any conventional group known to protect a basic nitrogen in standard synthetic procedures.

Leaving groups suitable for use in the inventive process include Cl, Br, I, OH, tosyl, mesyl or the like, preferably OH or tosyl.

Bases suitable for use as the first base in the process of the invention include strong bases such as NaH, KOt-Bu, NaOH or any conventional base capable of removing a proton from an azaindole or azaindazole nitrogen atom.

Bases suitable for use as the second base in the inventive process include weak bases such as $K_2CO_3$, $Na_2CO_3$, tertiary organic amines such as triethylamine or the like.

Conditions for the deprotection step may vary depending upon the nature of the protecting group. For example, for a t-butyl carboxylate protecting group, deprotection may take place in the presence of an acid such as trifluoroacetic acid or HCl and optionally an aprotic solvent such as dioxane. When a benzyl group is used as the protecting group, deprotection may take place via catalytic hydrogenation.

Compounds of formula II wherein W is $CR_2$ (IIa) may be prepared using conventional synthetic methods and, if required, standard separation and isolation techniques. For example, a nitropyridine compound of formula V may be reacted with a chloromethylsulfonyl compound of formula VI in the presence of a strong base to give the intermediate of formula VII said formula VII intermediate may then be treated with a reducing agent such as Fe, Zn or Sn in the presence of an acid to give the amine of formula VIII; said amine may then be reacted with the appropriate orthoester of formula IX to give the formula X compound; and said compound may be cyclized in the presence of a base to give the desired formula IIa 3-sulfonyl azaindole. The synthetic method is described by W. Wojciechowski and M. Makosza, Synthesis 1986, 651–653. Similarly, the formula VIII amine may be reacted with $NaNO_2$ in the presence of an acid to give those compounds of formula II wherein W is N (IIb). The reaction sequences are shown in flow diagram II.

Flow Diagram II

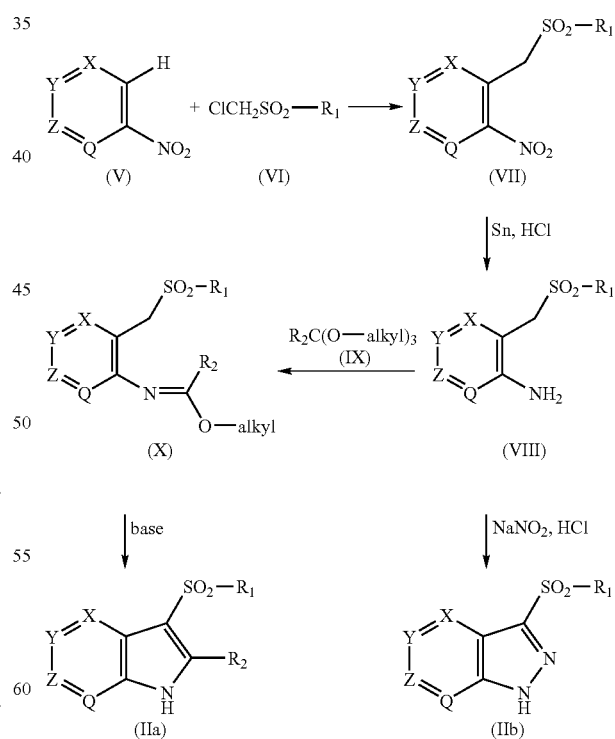

Alternatively, compounds of formula II may be prepared directly from the azaindazole or azaindole compound of formula XI by reacting said formula XI compound with iodine optionally in the presence of KI to give the corresponding 3-iodo compound of formula XII, coupling said 3-iodo compound with a thiol of formula XIII to give the corresponding 3-thio derivative of formula XIV and oxidizing said thio compound using conventional oxidizing agents such as H₂O₂, m-chloroperbenzoic acid, or the like to give the desired formula II intermediate. The reaction is shown in flow diagram III.

Flow Diagram III

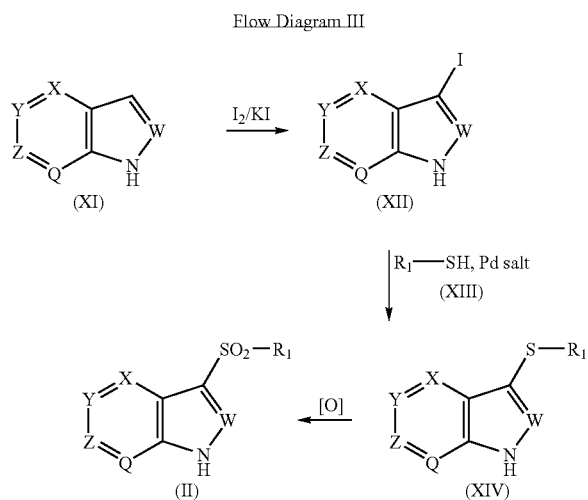

The formula XIV 3-thio derivative may also be prepared in a single step from the appropriate compound of formula XI by reacting said formula XI compound with a suitable thiol of formula XIII in the presence of iodine, preferably in a polar solvent such as aqueous alcohol. The thus-obtained formula II compounds may then be carried on to the desired compounds of formula I as shown in flow diagram I.

Compounds of formula I wherein n is 0 and W is CR₂ (Ia) may be prepared by the reductive amination of a compound of formula VIII with a protected azinone of formula XV to give the protected compound of formula XVI. The formula XVI compound is reacted with an N,N-dialkylamide-dialkoxy acetal to give the compound of formula XVII, which is cyclized in the presence of an acid to give the protected precursor of formula XVIII. The formula XVIII precursor may then be deprotected and optionally alkylated as shown in flow diagram I to give the desired formula Ia products. The reaction is shown in flow diagram IV wherein P represents a protecting group, L' represents a leaving group and R' and R" are each independently C₁–C₃alkyl.

Flow Diagram IV

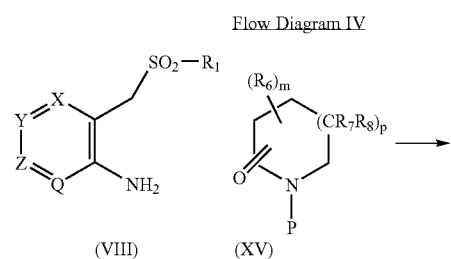

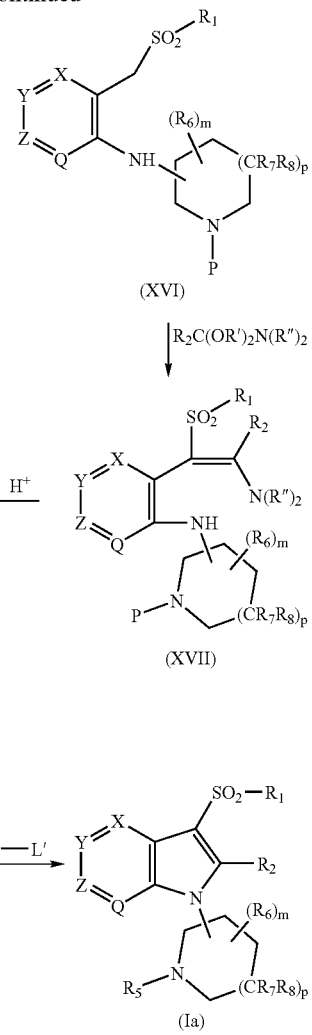

Alternatively, compounds of formula Ia may be prepared by condensing the protected azinone compound of formula XV with a heterocyclic amine of formula XIX to give the corresponding imine derivative of formula XX, reducing the formula XX imine with sodium borohydride to give the amine compound of formula XXI and converting said amine to the ring-closed product of formula XXII via standard ring formation techniques, for example, formylation/acylation of the formula XXI amine followed by cyclization under basic conditions to give the compound of formula XXII wherein W is CR₂; or the N-nitrosation of the formula XXI amine followed by reduction and cyclization to give the ring-closed product of formula XXII wherein W is N. Said formula XXII compound may then be reacted with a sulfonyl chloride of formula XXIII in the presence of a reagent such as silver trifluoromethanesulfonate (AgOTf) to give the 3-sulfonylindazole or indole compound of formula XXIV. Deprotection and optional alkylation of the formula XXIV compound as shown hereinabove in flow diagram I gives the desired compound of formula Ia. The reaction is shown in flow diagram V wherein P represents a protecting group and L' represents a leaving group, as described hereinabove.

diagram I to give the desired formula Ib products. The reaction is shown in flow diagram VI wherein P represents a protecting group and L' represents a leaving group, as described hereinabove.

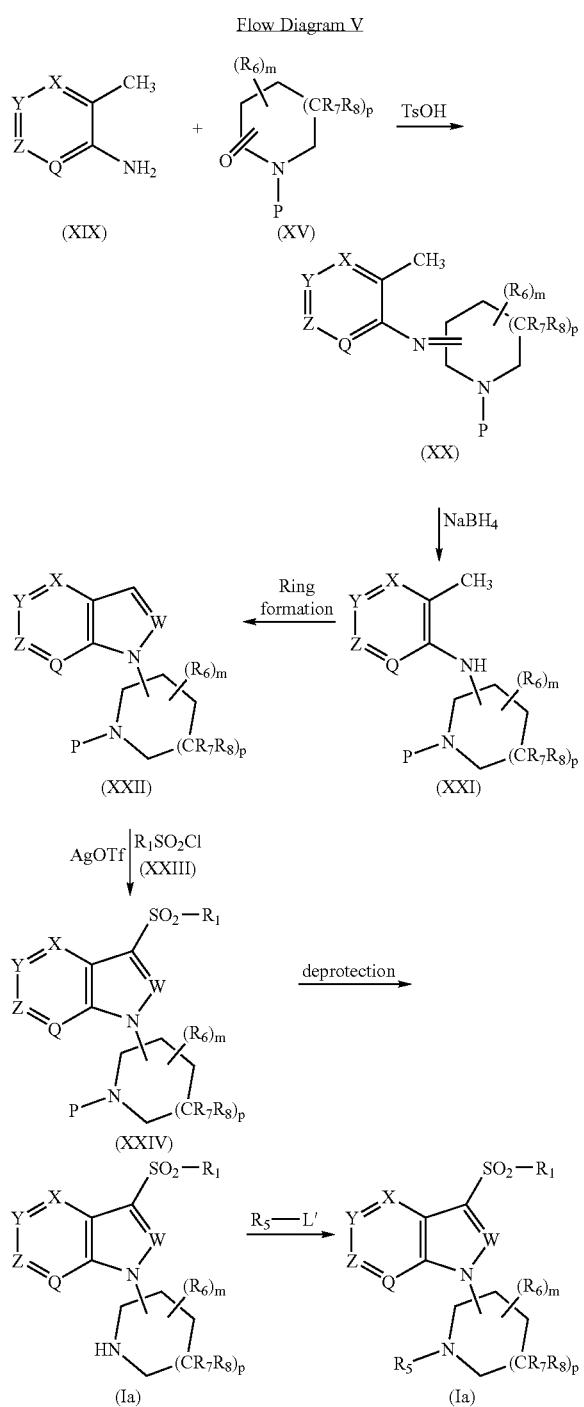

Flow Diagram V

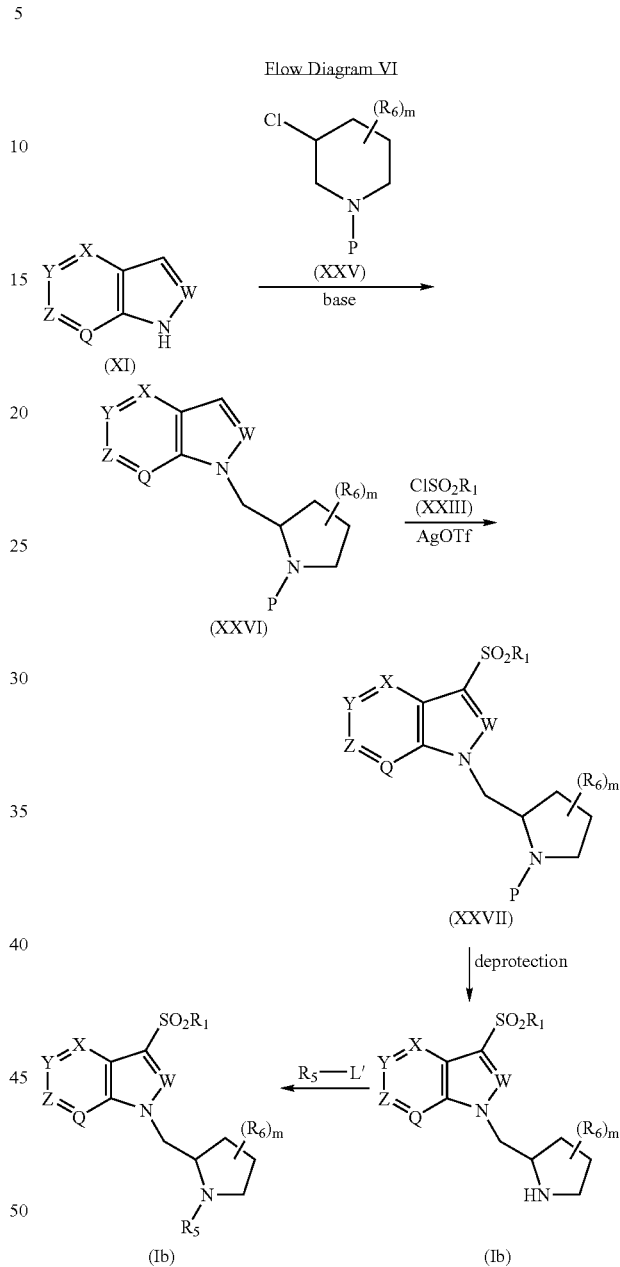

Flow Diagram VI

Compounds of formula I wherein n is 1, p is 0 and the pyrrolidine ring is attached in the 2-position (Ib) may be prepared by reacting the azaindazole or azaindole compound of formula XI with a 3-chloropiperidine derivative of formula XXV in the presence of a base such as a carbonate, i.e. potassium or cesium carbonate to give the 1-pyrrolidinyl-methyl compound of formula XXVI and reacting said formula XXVI compound with the sulfonyl chloride of formula XXIII to give the 3-sulfonylindazole or indole compound of formula XXVII. The formula XXVII compound may then be deprotected and optionally alkylated as shown in flow Advantageously, the formula I compounds of the invention are useful for the treatment of CNS disorders related to or affected by 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HNMR designates proton nuclear magnetic resonance. The terms DMF and DMSO designate dimethyl formamide and dimethylsulfoxide, respectively. All chromatography is performed using $SiO_2$ as support.

EXAMPLE 1

Preparation of 3-(Phenylthio)-1H-pyrrolo[2,3-b]pyridine

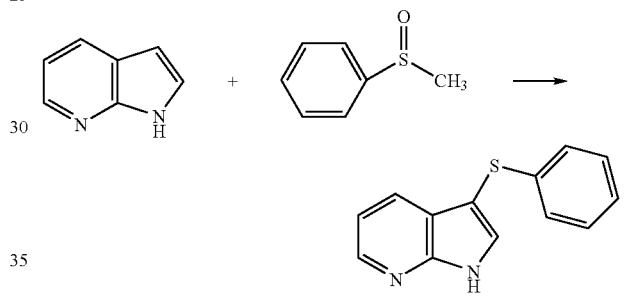

A solution of methyl phenyl sulfoxide (8.33 g, 59.4 mmol) in $CH_2Cl_2$ is chilled to −78° C. and treated dropwise with trifluoroacetic anhydride (4.1 mL, 5.3 mmol). After stirring for 30 min at −78° C., a solution of 7-azaindole (5.2 g, 44.0 mmol) in $CH_2Cl_2$ is added. After 30 min at −78° C., triethylamine (74 mL, 534 mmol) is added and the reaction is allowed to reach ambient temperature. After stirring for 3.5 days, the reaction is concentrated in vacuo, treated with saturated aqueous $NaHCO_3$ and extracted with $CH_2Cl_2$. The organic extracts are combined and concentrated in vacuo. The resultant residue is crystallized from methanol/$H_2O$ and recrystallized from $CH_2Cl_2$/hexane to afford the title compound as an off-white solid, 1.26 g, mp 188–189° C., characterized by mass spectral analyses and HNMR analyses.

EXAMPLE 2

Preparation of 3-(Phenylsulfonyl)-1H-pyrrolo[2,3-b]pyridine

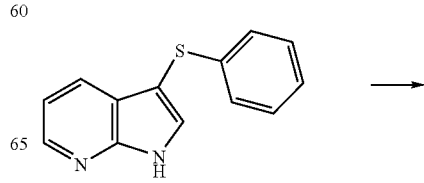

-continued

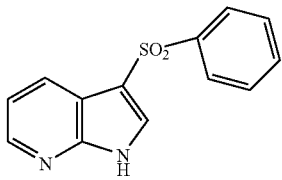

A solution of 3-(phenylthio)-1H-pyrrolo[2,3-b]pyridine (100 mg, 0.44 mmol) in t-butyl alcohol is treated with MnSO$_4$·H$_2$O (4 mg, 0.020 mmol) and cooled to 0° C. A mixture of 30% aqueous hydrogen peroxide (500 mg, 4.41 mmol) and 0.2 N aqueous NaHCO$_3$ (7.5 mL) is added dropwise. The reaction is stirred for 23 h at 20° C., diluted with saturated aqueous NaHCO$_3$ and extracted with ethyl acetate. The combined extracts are dried over MgSO$_4$ and concentrated in vacuo. Chromatography (1:50 methanol: CH$_2$Cl$_2$) of the resultant residue yields a solid product which is recrystallized from CH$_2$Cl$_2$/hexane to afford the title compound as a pinkish-white solid, 58 mg, mp>250° C., characterized by mass spectral and HNMR analyses.

EXAMPLE 3

Preparation of 3-(Phenylsulfonyl)-1-[(2R)-pyrrolidin-2-yl-methyl]-1H-pyrrolo[2,3-b]pyridine Hydrochloride

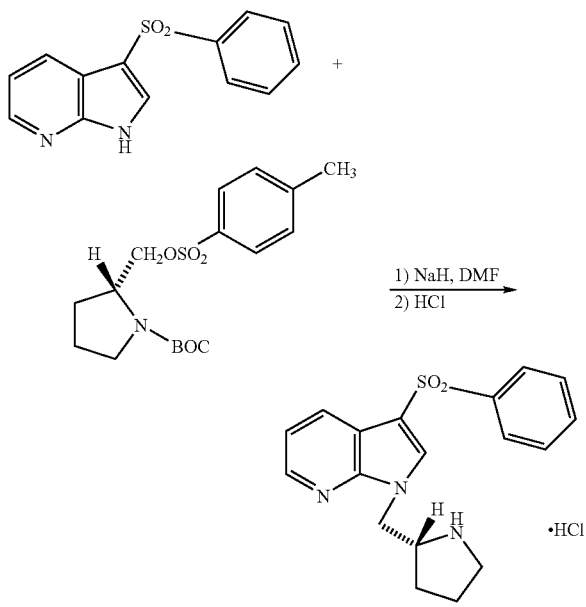

A stirred solution of 3-(phenylsulfonyl)-1H-pyrrolo[2,3-b]pyridine (750 mg, 2.90 mmol) in anhydrous DMF is chilled to 0° C., treated with 60% NaH in mineral oil (173 mg, 4.35 mmol), stirred for 1 h at ambient temperatures, cooled to 0° C., treated with a solution of tert-butyl (2R)-2-({[4-methylphenyl)sulfonyl]oxy}methyl)-1-pyrrolidinecarboxylate[1] (2.24 g, 6.30 mmol) in anhydrous DMF, heated at 45° C. for 45 h, cooled to 0° C., treated with H$_2$O and brine and extracted with ethyl acetate. The combined extracts are dried over MgSO$_4$ and concentrated in vacuo. The resultant residue is chromatographed (1:3 ether:hexanes) to afford the BOC-protected intermediate as a clear gum. The gum is dissolved in dioxane, treated with 4M HCl in dioxane (12.4 mL, 49.6 mmol), stirred for 4 h at ambient temperatures and concentrated in vacuo. The resultant residue is crystallized from ethanol/ether to afford the title compound as a white solid 665 mg, (57% yield), mp 194°–196° C., [a]$^{20}_D$=–18.16, characterized by HNMR and mass spectral analyses.

[1] U.S. Pat. No. 6,180,627

EXAMPLE 4

Preparation of 3-(Phenylsulfonyl)-1-[(2S)-pyrrolidin-2-ylmethyl]-1H-pyrrolo[2,3-b]pyridine Hydrochloride

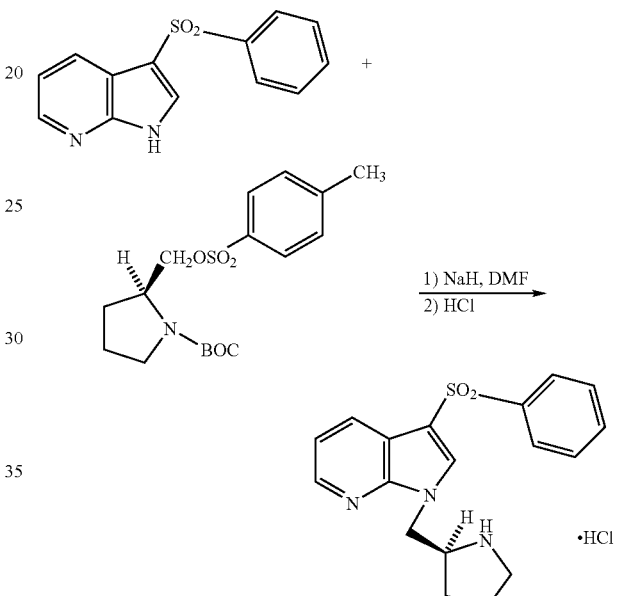

Using essentially the same procedure described in Example 3 and employing t-butyl (2S)-2-{{[(4-methylphenyl)sulfonyl]oxy}methyl}-1-pyrrolidinecarboxylate[2] as reagent, the title product is obtained as a white solid, 656 mg (56% yield), mp 194°–196° C., [a]$^{20}_D$=+18.88, identified by HNMR and mass spectral analyses.

[2] K. Jones and W. King-Chung Woo, Tetrahedron, 1991 (47), 7179–7184.

EXAMPLE 5

Preparation of 1-[(1-Benzylpyrrolidin-2-yl)methyl]-1H-pyrrolo[2,3-b]pyridine

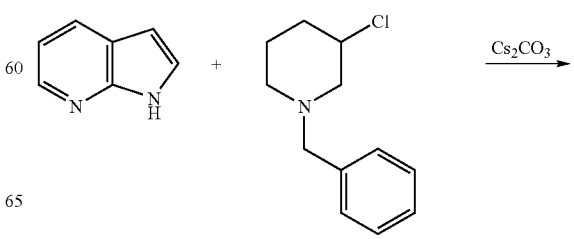

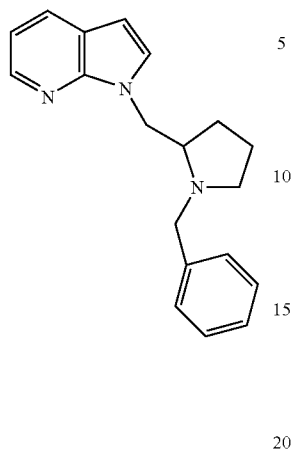

A mixture of 1-benzyl-3-chloropiperidine (3.83 g, 18.3 mmol), 1H-pyrrolo[2,3-b]pyridine (4.4 g, 36.5 mmol) and cesium carbonate (17.8 g, 54.8 mmol) in DMSO is stirred at 80° C. under a nitrogen atmosphere for 24 h. The reaction is monitored by thin layer chromatography. Two additional amounts of 1-benzyl-3-chloro-piperidine (3.83 g and 1.91 g) are added at 12 h intervals. After 48 h, the mixture is cooled, treated with water and extracted with ethyl acetate. The extracts are combined, washed sequentially with water and brine and concentrated in vacuo. The resultant residue is purified by flash chromatography (4–5% methanol in $CH_2Cl_2$ as eluent) to afford the title compound as an oil, 6.5 g (60% yield), identified by HNMR and mass spectral analyses.

EXAMPLE 6

Preparation of 1-[(1-Benzylpyrrolidin-2-yl)methyl]-3-(3-chlorophenylsulfonyl)-1H-pyrrolo[2,3-b]pyridine

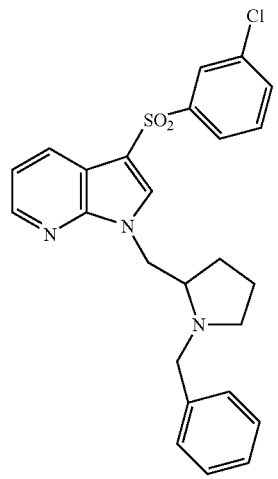

A mixture of 1-[(1-benzylpyrrolidin-2-yl)methyl]-1H-pyrrolo[2,3-b]pyridine (2.0 g, 6.86 mmol), 3-chlorophenylsulfonyl chloride (1.63 g, 7.55 mmol) and silver trifluoromethanesulfonate (AgOTf) (2.32 g, 8.92 mmol) in nitrobenzene is heated at 100° C. under a nitrogen atmosphere for 36 h, cooled to room temperature, quenched with 10% aqueous sodium carbonate, and extracted with $CH_2Cl_2$. The extracts are combined, washed sequentially with water and brine and concentrated in vacuo. The resultant residue is purified by flash column chromatography (0–5% methanol in $CH_2Cl_2$ as eluent) to afford the title compound as a semi-solid, 865 mg (27% yield), identified by HNMR and mass spectral analyses.

EXAMPLE 7

Preparation of 3-(3-Chlorophenylsulfonyl)-1-(pyrrolidin-2-ylmethyl)-1H-pyrrolo[2,3-b]pyridine

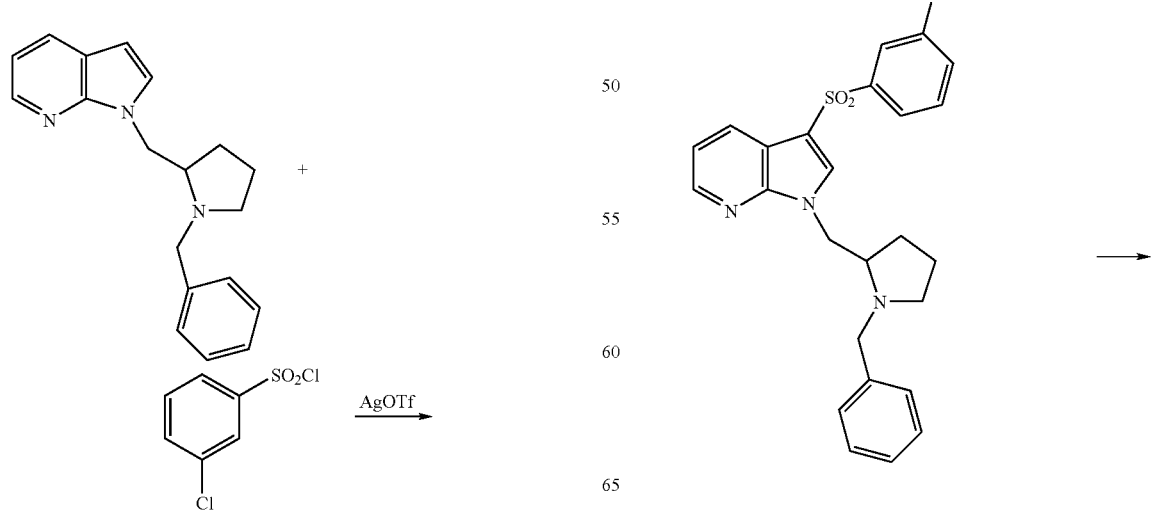

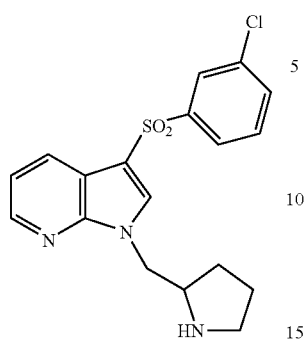

A stirred solution of 1-[(1-benzyl-pyrrolidin-2-yl)methyl]-3-(3-chlorophenyl-sulfonyl)-1H-pyrrolo[2,3-b]pyridine (0.812 g, 1.74 mmol) in 1,2-dichloroethane under a nitrogen atmosphere is treated with 1-chloroethylchloroformate (0.47 mL, 4.35 mmol); heated at reflux temperature until the disappearance of starting material by thin layer chromatography (3 h), cooled and concentrated in vacuo. The resultant residue is dissolved in CH$_2$Cl$_2$ and re-evaporated twice. This residue is dissolved in ethanol, heated at reflux temperature for 1.5 h, cooled to room temperature, diluted with water, and extracted with ethyl acetate. The extracts are combined, washed sequentially with water and brine, and concentrated in vacuo. The final residue is purified by flash column chromatography (10–15% methanol in CH$_2$Cl$_2$ as eluent) to afford the title compound as an oil, 443 mg (68% yield), identified by HNMR and mass spectral analyses.

EXAMPLE 8

Preparation of 3-(3-Chlorophenylsulfonyl)-1-[(1-methylpyrrolidin-2-yl)methyl]-1H-pyrrolo[2,3

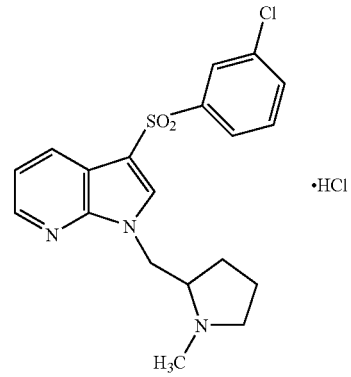

A suspension of 3-(3-chlorophenylsulfonyl)-1-(pyrrolidin-2-ylmethyl)-1H-pyrrolo[2,3-b]pyridine (0.09 g, 0.24 mmol) in DMF under a nitrogen atmosphere at room temperature is treated with iodomethane (0.021 mL, 0.34 mmol), stirred at room temperature for 18 h, diluted with water and extracted with ethyl acetate. The extracts are combined, washed sequentially with water and brine and concentrated in vacuo. The resultant residue is purified by flash chromatography (5% methanol in CH$_2$Cl$_2$ as eluent) to afford the free amine of the title product. The amine is dissolved in Et$_2$O, treated with an etheral solution of anhydrous HCl, stirred and concentrated in vacuo to afford the title compound as a solid, 30 mg, mp 149–150° C., identified by HNMR and mass spectral analyses.

EXAMPLES 9–16

Preparation of 3-(3-Arylsulfonyl)-1-(pyrrolidin-2-ylmethly)-1H-pyrrolo[2,3-b]-pyridine Hydrochloride Derivatives Using essentially the same procedures described in Examples 5–8 hereinabove and employing the appropriate aryl- or heteroarylsulfonyl chloride and 1-[(1-benzylpyrrolidin-2-yl)methyl]-1H-pyrrolo[2,3-b]pyridine substrate, the compounds shown on Table I are obtained and identified by HNMR and mass spectral analyses.

TABLE I

| EX No | R1 | R5 | mp °C. |
|---|---|---|---|
| 9 | $C_6H_5$ | $CH_2C_6H_5$ | 218–220 |
| 10 | 3-F—$C_6H_5$ | $CH_2C_6H_5$ | 128–129 |
| 11 | 3-F—$C_6H_5$ | H | 181–182 |
| 12 | 3-F—$C_6H_5$ | $CH_3$ | 208–209 |
| 13 | 6-Cl-imidazo[2,1-b][1,3]thiazol-5-yl | $CH_2C_6H_5$ | 102–103* |
| 14 | 6-Cl-imidazo[2,1-b][1,3]thiazol-5-yl | H | 246–247 |
| 15 | 5-Cl-thien-2-yl | H | 106–107 |
| 16 | 5-Cl-thien-2-yl | $CH_2C_6H_5$ | 141–142 |

*Free amine

EXAMPLE 17

Preparation of 1-[(1-Methylpyrrolidin-2-yl)methyl]-1H-pyrrolo[2,3-b]pyridine (A) and 1-(1-Methylpiperidin-3-yl)-1H-pyrrolo[2,3-b]pyridine (B)

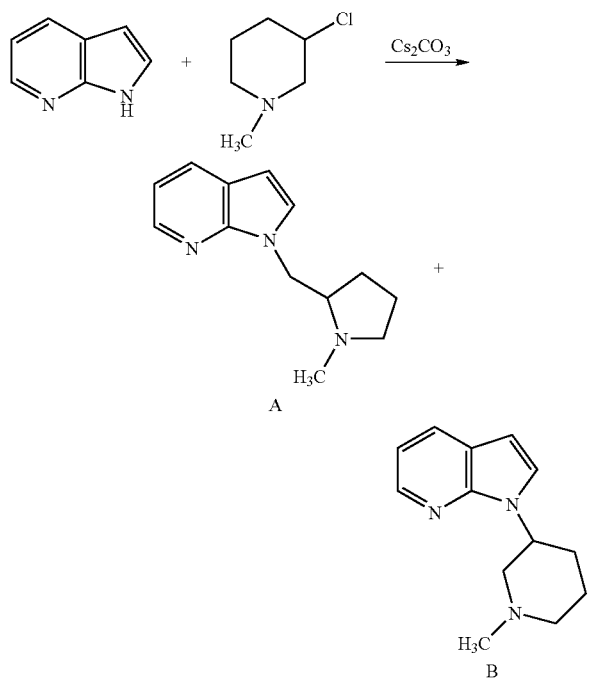

A mixture of 3-chloro-1-methylpiperidine (0.5 g, 3.75 mmol), 1H-pyrrolo[2,3-b]pyridine (0.904 g, 7.5 mmol) and cesium carbonate (2.44 g, 7.5 mmol) in DMSO is stirred at 80° C. for 24 h, treated with another portion of 3-chloro-1-methylpiperidine (0.5 g, 3.75 mmol), stirred at 80° C. for another 24 h, treated with a third portion of 3-chloro-1-methylpiperidine (0.25 g, 1.9 mmol), stirred at 80° C. for another 24 h until the disappearance of the pyrrolopyridine starting material by thin layer chromatography. The reaction mixture is cooled, treated with water and extracted with ethyl acetate. The extracts are combined, washed sequentially with water and brine and concentrated in vacuo. The resultant mixture is purified by flash chromatography (9:1 $CH_2Cl_2$/methanol as eluent) to afford the title product A as an oil, 0.77 g, identified by HNMR and mass spectral analyses; and the title product B as an oil, 0.56 g, identified by HNMR and mass spectral analyses.

EXAMPLE 18

Preparation of 3-[(6-chloroimidazo[2.1-b][1,3]thiazol-5-yl)sulfonyl]-1-(1-methylpiperidin-3-yl))-1H-pyrrolo[2,3-b]pyridine;

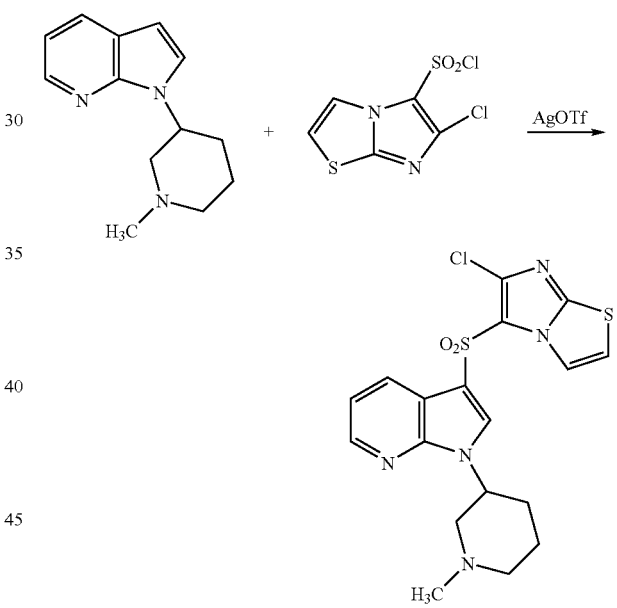

Using essentially the same procedure described in Example 6 and employing 6-chloroimidazo[2,1-b][1,3]thiazol-5-ylsulfonyl chloride and 1-(1-methylpiperidin-3-yl))-1H-pyrrolo[2,3-b]pyridine as starting materials, the title product is obtained and identified by HNMR and mass spectral analyses.

EXAMPLE 19

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTop-Count® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table II, below.

TABLE II

| Test Compound (Ex. No.) | 5-HT6 Binding Ki (nM) |
|---|---|
| 3 | 12 |
| 4 | 66 |
| 6 | 132 |
| 7 | 3 |
| 8 | 7 |
| 9 | 163 |
| 10 | 174 |
| 11 | 9 |
| 12 | 6 |
| 13 | 57 |
| 14 | 2 |
| 15 | 7 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

What is claimed is:

1. A compound of formula I

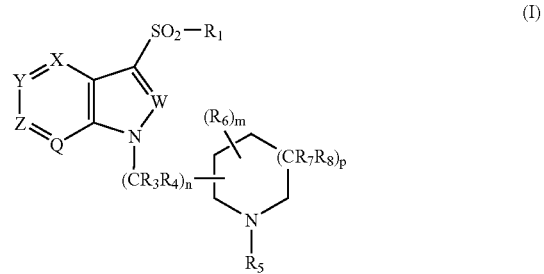

wherein

W is $CR_2$;

X is N or $CR_9$;

Y is N or $CR_{10}$;

Z is N or $CR_{11}$;

Q is N or $CR_{12}$ with the proviso that at least one and not more than two of X, Y, Z and Q must be N;

$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_2$ is H, halogen, or a $C_1$–$C_6$alkyl, $C_1$–$C_6$alkoxy, $C_3$–$C_7$cycloalkyl, aryl or heteroaryl group each optionally substituted;

$R_3$ and $R_4$ are each independently H or an optionally substituted $C_1$–$C_6$alkyl group;

$R_5$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

$R_6$ is a $C_1$–$C_6$alkyl, $C_3$–$C_7$cycloalkyl, $C_2$–$C_6$alkenyl or $C_2$–$C_6$alkynyl group each optionally substituted;

R₇ and R₈ are each independently H or a $C_1$–$C_6$alkyl, $C_3$–$C_7$cycloalkyl, $C_2$–$C_6$alkenyl or $C_2$–$C_6$alkynyl group each optionally substituted;

m and n are each independently 0 or an integer of 1, 2 or 3;

p is 0 or an integer of 1 or 2;

$R_9$, $R_{10}$, $R_{11}$ and $R_{12}$ are each independently H, halogen, CN, $OCO_2R_{13}$, $CO_2R_{14}$, $CONR_{15}R_{16}$, $SO_xR_{17}$, $NR_{18}R_{19}$, $OR_{20}$, $COR_{21}$ or a $C_1$–$C_6$alkyl, $C_2$–$C_6$alkenyl, $C_2$–$C_6$alkynyl, $C_3$–$C_7$cycloalkyl, aryl or heteroaryl group each optionally substituted;

$R_{13}$, $R_{14}$, $R_{17}$ and $R_{21}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{15}$, $R_{16}$, $R_{18}$ and $R_{19}$ are each independently H or an optionally substituted $C_1$–$C_4$alkyl group or $R_{15}$ and $R_{16}$ or $R_{18}$ and $R_{19}$ may be taken together with the atom to which they are attached to form a 5- to 7-membered ring optionally containing another heteroatom selected from O, $NR_{22}$ or $SO_q$;

$R_{20}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

x and q are each independently 0 or an integer of 1 or 2; and $R_{22}$ is H or a $C_1$–$C_6$alkyl, $C_2$–$C_6$alkenyl, $C_2$–$C_6$alkynyl, $C_3$–$C_7$cycloalkyl, cycloheteroalkyl aryl or heteraryl group each optionally substituted; or the stereoisomers thereof or the pharmaceutically acceptable salts thereof.

2. The compound according to claim 1 wherein n is 0 or 1.

3. The compound according to claim 1 wherein $R_5$ is H or methyl.

4. The compound according to claim 1 wherein $R_1$ is an optionally substituted phenyl, thienyl or imidazothiazolyl group.

5. The compound according to claim 2 wherein p is 0 or 1.

6. The compound according to claim 2 wherein m is 0.

7. The compound according to claim 5 wherein the piperidinyl group is attached in the 3-position of the piperidine ring or the pyrrolidinyl group is attached in the 2-position of the pyrrolidine ring.

8. The compound according to claim 7 wherein $R_5$ is H or methyl and $R_1$ is an optionally substituted phenyl, thienyl or imidazothiazolyl group.

9. The compound according to claim 1 selected from the group consisting of:
3-(phenylsulfonyl)-1-[(2R)-pyrrolidin-2-ylmethyl]-1H-pyrrolo[2,3-b]pyridine;
3-(phenylsulfonyl)-1-[(2S)-pyrrolidin-2-ylmethyl]-1H-pyrrolo[2,3-b]pyridine;
3-[(4-methylphenyl)sulfonyl]-1-(piperidin-4-ylmethyl)-1H-pyrrolo[2,3-b]pyridine;
6-bromo-3-(phenylsulfonyl)-1-(piperidin-4-ylmethyl)-1H-pyrrolo[2,3-c]pyridine;
7-methoxy-3-(phenylsulfonyl)-1-(piperidin-4-ylmethyl)-1H-pyrrolo[2,3]-c]pyridine;
6-hydroxy-3-(phenylsulfonyl)-1-(piperidin-4-ylmethyl)-1H-pyrrolo[3,2-b]pyridine;
6-chloro-3-[(4-fluorophenyl)sulfonyl]-1-(piperidin-4-ylmethyl)-1H-pyrrolo[2,3-c]pyridine;
6-fluoro-3-[(3-fluorophenyl)sulfonyl]-1-(piperidin-4-ylmethyl)-1H-pyrrolo[3,2-b]pyridine; 5-chloro-3-[(3-chlorophenyl)sulfonyl]-1-(piperidin-4-ylmethyl)-1H-pyrrolo[3,2-c]pyridine; 3-[(2-chlorophenyl)sulfonyl]-6-fluoro-1-(piperidin-4-ylmethyl)-1H-pyrrolo[2,3-c]pyridine;
3-[(2-fluorophenyl)sulfonyl]-6-methoxy-1-(piperidin-4-ylmethyl)-1H-pyrrolo[3,2-b]pyridine;
4-chloro-3-(phenylsulfonyl)-1-(piperidin-3-ylmethyl)-1H-pyrrolo[2,3-b]pyridine;
7-methoxy-3-(phenylsulfonyl)-1-(piperidin-3-ylmethyl)-1H-pyrrolo[2,3-c]pyridine; 6-hydroxy-3-(phenylsulfonyl)-1-(piperidin-3-ylmethyl)-1H-pyrrolo[3,2-b]pyridine; 6-chloro-3-[(4-fluorophenyl)sulfonyl]-1-(piperidin-2-ylmethyl)-1H-pyrrolo[3,2-c]pyridine;
6-fluoro-3-[(3-fluorophenyl)sulfonyl]-1-(piperidin-2-ylmethyl)-1H-pyrrolo[2,3-b]pyridine;
5-chloro-3-[(3-chlorophenyl)sulfonyl]-1-(piperidin-2-ylmethyl)-1H-pyrrolo[2,3-c]pyridine;
3-[(2-chlorophenyl)sulfonyl]-6-fluoro-1-(piperidin-2-ylmethyl)-1H-pyrrolo[3,2-b]pyridine;
3-[(2-fluorophenyl)sulfonyl]-6-methoxy-1-(piperidin-2-ylmethyl)-1H-pyrrolo[3,2-c]pyridine;
6-bromo-3-(phenylsulfonyl)-1-(pyrrolidin-3-ylmethyl)-1H-pyrrolo[3,2-c]pyridine;
4-chloro-2-methyl-3-(phenylsulfonyl)-1-(pyrrolidin-2-ylmethyl)-1H-pyrrolo[2,3-b]pyridine;
7-methoxy-3-(phenylsulfonyl)-1-(pyrrolidin-2-ylmethyl)-1H-pyrrolo[2,3-c]pyridine;
6-hydroxy-3-(phenylsulfonyl)-1-(pyrrolidin-2-ylmethyl)-1H-pyrrolo[3,2-b]pyridine;
1-(piperidin-2-ylmethyl)-3-(2-pyridinylsulfonyl)-1H-pyrrolo[3,2-c]pyridine;
1-(piperidin-3-ylmethyl)-3-(2-pyridinylsulfonyl)-1H-pyrrolo[2,3-b]pyridine;
3-(2-pyridinylsulfonyl)-1-(pyrrolidin-3-ylmethyl)-1H-pyrrolo[2,3-c]pyridine;
1-(1-phenethylpyrrolidin-3-yl)-3-(phenylsulfonyl)-1H-pyrrolo[3,2-c]pyridine;
1-piperidin-4-yl-3-(2-pyridylsulfonyl)-1H-pyrrolo[2,3-c]pyridine;
1-piperidin-3-yl-3-(2-thienyisulfonyl)-1H-pyrrolo[3,2-b]pyridine;
1-pyrrolidin-3-yl-3-(3-thienylsulfonyl)-1H-pyrrolo[3,2-b]pyridine;
1-[(1-benzylpyrrolidin-2-yl)methyl]-3-(phenylsulfonyl)-1H-pyrrolo[2,3-b]pyridine;
3-(phenylsulfonyl)-1-(pyrrolidin-2-ylmethyl)-1H-pyrrolo[2,3-b]pyridine;
1-[(1-benzylpyrrolidin-2-yl)methyl]-3-(3-fluorophenylsulfonyl)-1H-pyrrolo[2,3-b]-pyridine;
3-(3-fluorophenylsulfonyl)-1-(pyrrolidin-2-ylmethyl)-1H-pyrrolo[2,3-b]pyridine;
1-[(1-benzylpyrrolidin-2-yl)methyl]-3-(3-chlorophenylsulfonyl)-1H-pyrrolo[2,3-b]-pyridine;
3-(3-chlorophenylsulfonyl)-1-(pyrrolidin-2-ylmethyl)-1H-pyrrolo[2,3-b]pyridine;
3-(3-chlorophenylsulfonyl)-1-[(1-methylpyrrolidin-2-yl)methyl]-1H-pyrrolo[2,3-b]pyridine;
3-[(6-chloroimidazo[2,1-b][1,3]thiazol-5-yl)sulfonyl]-1-(pyrrolidin-2-ylmethyl)-1H-pyrrolo[2,3-b]pyridine;
3-[(6-chloroimidazo[2,1-b][1,3]thiazot-5-yl)sulfonyl]-1-(1-methylpiperidin-3-yl))-1 H-pyrrolo[2,3-b]pyridine;
3-[(6-chloroimidazo[2,1-b][1,3]thiazol-5-yl)sulfonyl]-1-(piperidin-3-yl))-1H-pyrrolo[2,3-b]pyridine;
3-[(6-chlorothien-2-yl)sulfonyl]-1-(pyrrolidin-2-ylmethyl)-1H-pyrrolo[2,3-b]pyridine;

the stereoisomers thereof; and
the pharmaceutically acceptable salts thereof.

10. A pharmaceutical composition which comprises a pharmaceutically acceptable carrier and an effective amount of a compound of formula I

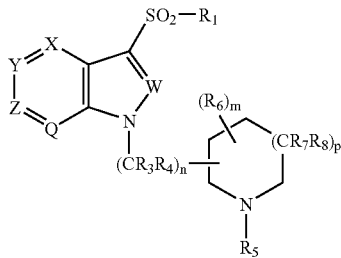

wherein
W is $CR_2$;
X is N or $CR_9$;
Y is N or $CR_{10}$;
Z is N or $CR_{11}$;
Q is N or $CR_{12}$ with the proviso that at least one and not more than two of X, Y, Z and Q must be N;
$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1,2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or heteroaryl group each optionally substituted;
$R_3$ and $R_4$ are each independently H or an optionally substituted $C_1$–$C_6$alkyl group;
$R_5$ is H or a $C_1$–$C6$alkyl, $C2$–$C6$alkynyl, $C3$–$C_7$cycloalkyl, cycloheteroalkyl, aryl or heteroaryl group each optionally substituted;
$R_6$ is a $C_1$–$C_6$alkyl, $C_3$–$C_7$cycloalkyl, $C_2$–$C_6$alkenyl or $C_2$–$C_6$alkynyl group each optionally substituted;
$R_7$ and $R_8$ are each independently H or a $C_1$–$C_6$alkyl, $C_3$–$C_7$cycloalkyl, $C_2$–$C_6$alkenyl or $C_2$–$C_6$alkynyl group each optionally substituted;
m and n are each independently 0 or an integer of 1, 2 or 3;
p is 0 or an integer of 1 or 2;
$R_9$, $R_{10}$, $R_{11}$ and $R_{12}$ are each independently H, halogen, CN, $OCO_2R_{13}$, $CO_2R_{14}$, $CONR_{15}R_{16}$, $SO_xR_{17}$, $NR_{18}R_{19}$, $OR_{20}$, $COR_{21}$ or a $C_1$–$C_6$alkyl, $C_2$–$C_6$alkenyl, $C_2$–$C_6$alkynyl, $C_3$–$C_7$cycloalkyl, aryl or heteroaryl group each optionally substituted;
$R_{13}$, $R_{14}$, $R_{17}$ and $R_{21}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{15}$, $R_{16}$, $R_{18}$ and $R_{19}$ are each independently H or an optionally substituted $C_1$–$C_4$alkyl group or $R_{15}$ and $R_{16}$ or $R_{18}$ and $R_{19}$ may be taken together with the atom to which they are attached to form a 5- to 7-membered ring optionally containing another heteroatom selected from O, $NR_{22}$ or $SO_q$;
$R_{20}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
x and q are each independently 0 or an integer of 1 or 2; and $R_{22}$ is H or a $C_1$–$C_6$alkyl, $C_2$–$C_6$alkenyl, $C2$–$C_6$alkynyl, $C_3$–$C_7$cycloalkyl, cycloheteroalky aryl or heteraryl group each optionally substituted; or the stereoisomers thereof or the pharmaceutically acceptable salts thereof.

11. The composition according to claim 10 having a formula I compound wherein n is 0 or 1.

12. The composition according to claim 11 having a formula I compound wherein $R_1$ is an optionally substituted phenyl, thienyl or imidazothiazolyl group and $R_5$ is H or methyl.

13. The composition according to claim 12 having a formula I compound wherein p is 0 or 1 and the piperidinyl group is attached in the 3-position of the piperidine ring or the pyrrolidinyl group is attached in the 2-position of the pyrrolidine ring.

14. The composition according to claim 10 having a formula I compound selected from the group consisting of:
3-(phenylsulfonyl)-1-[(2R)-pyrrolidin-2-ylmethyl]-1H-pyrrolo[2,3-b]pyridine;
3-(phenylsulfonyl)-1-[(2S)-pyrrolidin-2-ylmethyl]-1H-pyrrolo[2,3-b]pyridine;
3-[(4-methylphenyl)sulfonyl]-1-(piperidin-4-ylmethyl)-1H-pyrrolo[2,3-b]pyridine;
6-bromo-3-(phenylsulfonyl)-1-(piperidin-4-ylmethyl)-1H-pyrrolo[2,3-c]pyridine; 7-methoxy-3-(phenylsulfonyl)-1-(piperidin-4-ylmethyl)-1H-pyrrolo[2,3-c]pyridine;
6-hydroxy-3-(phenylsulfonyl)-1-(piperidin-4-ylmethyl)-1H-pyrrolo[3,2-b]pyridine;
6-chloro-3-[(4-fluorophenyl)sulfonyl]-1-(piperidin-4-ylmethyl) -1H-pyrrolo[2,3-c]pyridine;
6-fluoro-3-[(3-fluorophenyl)sulfonyl]-1-(piperidin-4-ylmethyl) -1H-pyrrolo[3,2-b]pyridine;
5-chloro-3-[(3-chlorophenyl)sulfonyl]-1-(piperidin-4-ylmethyl) -1H-pyrrolo[2,3-c]pyridine;
3-[(2-chlorophenyl)sulfonyl]-6-fluoro-1-(piperidin-4-ylmethyl) -1H-pyrrolo[2,3-c]pyridine;
3-[(2-fluorophenyl)sulfonyl]-6-methoxy-1-(piperidin-4-ylmethyl) -1H-pyrrolo[3,2-b]pyridine;
4-chloro-3-(phenylsulfonyl)-1-(piperidin-3-ylmethyl)-1H-pyrrolo[2,3-b]pyridine;
7-methoxy-3-(phenylsulfonyl)-1-(piperidin-3-ylmethyl)-1H-pyrrolo[2,3-c]pyridine;
6-hydroxy-3-(phenylsulfonyl)-1-(piperidin-3-ylmethyl)-1H-pyrrolo[3,2-b]pyridine;
6-chloro-3-[(4-fluorophenyl)sulfonyl]-1-(piperidin-2-ylmethyl)-1H-pyrrolo[3,2-c]pyridine;
6-fluoro-3-[(3-fluorophenyl)sulfonyl]-1-(piperidin-2-ylmethyl)-1H-pyrrolo[2,3-b]pyridine;
5-chloro-3-[(3-chlorophenyl)sulfonyl]-1-(piperidin-2-ylmethyl)-1H-pyrrolo[2,3-c]pyridine;
3-[(2-chlorophenyl)sulfonyl]-6-fluoro-1-(piperidin-2-ylmethyl)-1H-pyrrolo[3,2-b]pyridine;
3-[(2-fluorophenyl)sulfonyl]-6-methoxy-1-(piperidin-2-ylmethyl)-1H-pyrrolo[3,2-c]pyridine;
6-bromo-3-(phenylsulfonyl)-1-(pyrrolidin-3-ylmethyl)-1H-pyrrolo[3,2-c]pyridine;
4-chloro-2-methyl-3-(phenylsulfonyl)-1-(pyrrolidin-2-ylmethyl)-1H-pyrrolo[2,3-b]pyridine;
7-methoxy-3-(phenylsulfonyl)-1-(pyrrolidin-2-ylmethyl)-1H-pyrrolo[2,3-c]pyridine;
6-hydroxy-3-(phenylsulfonyl)-1-(pyrrolidin-2-ylmethyl)-1H-pyrrolo[3,2-b]pyridine;
1-(piperidin-2-ylmethyl)-3-(2-pyridinylsulfonyl)-1H-pyrrolo[3,2-c]pyridine;

1-(piperidin-3-ylmethyl)-3-(2-pyridinylsulfonyl)-1H-pyrrolo[2,3-b]pyridine;
3-(2-pyridinylsulfonyl)-1-(pyrrolidin-3-ylmethyl)-1H-pyrrolo[2,3-c]pyridine;
1-(1-phenethylpyrrolidin-3-yl)-3-(phenylsulfonyl)-1H-pyrrolo[3,2-c]pyridine;
1-piperidin-4-yl-3-(2-pyridylsulfonyl)-1H-pyrrolo[2,3-c]pyridine;
1-piperidin-3-yl-3-(2-thienylsulfonyl)-1H-pyrrolo[3,2-b]pyridine;
1-pyrrolidin-3-yl-3-(3-thienylsulfonyl)-1H-pyrrolo[3,2-b]pyridine;
1-[(1-benzylpyrrolidin-2-yl)methyl]-3-(phenylsulfonyl)-1H-pyrrolo[2,3-b]pyridine;
3-(phenylsulfonyl)-1-(pyrrolidin-2-ylmethyl)-1H-pyrrolo[2,3-b]pyridine;
1-[(1-benzylpyrrolidin-2-yl)methyl]-3-(3-fluorophenylsulfonyl)-1H-pyrrolo[2,3-b]-pyridine;
3-(3-fluorophenylsulfonyl)-1-(pyrrolidin-2-ylmethyl)-1H-pyrrolo[2,3-b]pyridine;
1-[(1-benzylpyrrolidin-2-yl)methyl]-3-(3-chlorophenylsulfonyl)-1H-pyrrolo[2,3-b]-pyridine;
3-(3-chlorophenylsulfonyl)-1-(pyrrolidin-2-ylmethyl)-1H-pyrrolo[2,3-b]pyridine;
3-(3-chlorophenylsulfonyl)-1-[(1-methylpyrrolidin-2-yl)methyl]-1H-pyrrolo[2,3-b]pyridine;
3-[(6-chloroimidazo[2,1-b][1,3]thiazol-5-yl)sulfonyl]-1-(pyrrolidin-2-ylmethyl)-1H-pyrrolo[2,3-b]pyridine;
3-[(6-chloroimidazo[2,1-b][1,3]thiazol-5-yl)sulfonyl]-1-(1-methylpiperidin-3-yl))-1H-pyrrolo[2,3-b]pyridine;
3-[(6-chloroimidazo[2,1-b][1,3]thiazol-5-yl)sulfonyl]-1-(piperidin-3-yl))-1H-pyrrolo[2,3-b]pyridine;
3-[(6-chlorothien-2-yl)sulfonyl]-1-(pyrrolidin-2-ylmethyl)-1H-pyrrolo[2,3-b]pyridine;

the stereoisomers thereof; and
the pharmaceutically acceptable salts thereof.

15. A process for the preparation of a compound of formula I

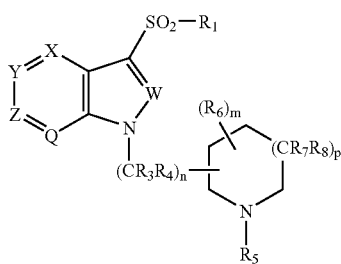

wherein
W is N or $CR_2$;
X is N or $CR_9$;
Y is N or $CR_{10}$;
Z is N or $CR_{11}$;
Q is N or $CR_{12}$ with the proviso that at least one and not more than two of X, Y, Z and Q must be N;
$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or heteroaryl group each optionally substituted;.
$R_3$ and $R_4$ are each independently H or an optionally substituted $C_1$–$C_6$alkyl group;
$R_5$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
$R_6$ is a $C_1$–$C_6$alkyl, $C_3$–$C_7$cycloalkyl, $C_{2–C6}$alkenyl or $C_2$–$C_6$alkynyl group each optionally substituted;
$R_7$ and $R_8$ are each independently H or a $C_1$–$C_6$alkyl, $C_3$–$C_7$cycloalkyl, $C_2$–$C_6$alkenyl or $C_2$–$C_6$alkynyl group each optionally substituted;
m and n are each independently 0 or an integer of 1, 2 or 3;
p is 0 or an integer of 1 or 2;
$R_9$, $R_{10}$, $R_{11}$ and $R_{12}$ are each independently H, halogen, CN, $OCO_2R_{13}$, $CO_2R_{14}$, $CONR_{15}R_{16}$, $SO_xR_{17}$, $NR_{18}R_{19}$, $OR_{20}$, $COR_{21}$ or a $C_1$–$C_6$alkyl, $C_2$–$C_6$alkenyl, $C_2$–$C_6$alkynyl, $C_3$–$C_7$cycloalkyl, aryl or heteroaryl group each optionally substituted;
$R_{13}$, $R_{14}$, $R_{17}$ and $R_{21}$ are each independently H or a $C_1$–$C_6$alkyl, $C_2$–$C_6$alkenyl, $C2$–$C_6$alkynyl, $C_3$–$C_6$cycloalkyl, cycloheteroalkyl, aryl or heteroaryl group each optionally substituted;
$R_{15}$, $R_{16}$, $R_{18}$ and $R_{19}$ are each independently H or an optionally substituted $C_1$–$C_4$alkyl group or $R_{15}$ and $R_{16}$ or $R_{18}$ and $R_{19}$ may be taken together with the atom to which they are attached to form a 5- to 7-membered ring optionally containing another heteroatom selected from O, $NR_{22}$ or $SO_q$;
$R_{20}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
x and q are each independently 0 or an integer of 1 or 2; and
$R_{22}$ is H or a $C_1$–$C_6$alkyl, $C_2$–$C_6$alkenyl, $C_2$–$C_6$alkynyl, $C_3$–$C_7$cycloalkyl, cycloheteroalky or heteraryl group each optionally substituted which process comprises reacting a compound of formula II

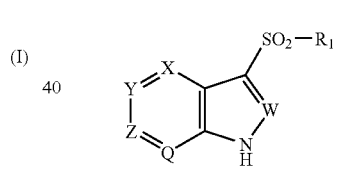

wherein W, X, Y, Z and Q are described hereinabove with a protected azacyclic compound of formula III

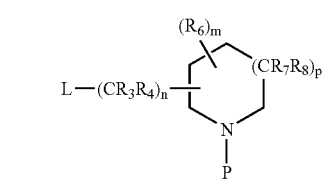

wherein L represents a leaving group; P represents a protecting group and $R_3$, $R_4$, $R_6$, $R_7$, $R_8$, n, m and p are as described hereinabove in the presence of a first base to give the protected amine of formula I; and deprotecting said amine to give the compound of formula I wherein $R_5$ is H optionally alkylating said formula I compound with a compound, $R_5$-L', wherein L' is a leaving group in the presence of a second base.

* * * * *